United States Patent
Lam et al.

(10) Patent No.: US 12,329,664 B2
(45) Date of Patent: *Jun. 17, 2025

(54) VESSEL PROSTHESIS

(71) Applicant: Terumo Corporation, Tokyo (JP)

(72) Inventors: Cang Lam, Tokyo (JP); Shirley Vong, Tokyo (JP); Priscilla Tsai, Tokyo (JP)

(73) Assignee: Terumo Corporation, Tokyo (JP)

( * ) Notice: Subject to any disclaimer, the term of this patent is extended or adjusted under 35 U.S.C. 154(b) by 350 days.

This patent is subject to a terminal disclaimer.

(21) Appl. No.: 17/336,157

(22) Filed: Jun. 1, 2021

(65) Prior Publication Data

US 2021/0282948 A1    Sep. 16, 2021

Related U.S. Application Data

(63) Continuation of application No. 16/428,677, filed on May 31, 2019, now Pat. No. 11,045,337, which is a continuation of application No. 15/268,379, filed on Sep. 16, 2016, now Pat. No. 10,335,299.

(60) Provisional application No. 62/220,895, filed on Sep. 18, 2015.

(51) Int. Cl.
*A61F 2/86* (2013.01)
*A61F 2/90* (2013.01)

(52) U.S. Cl.
CPC ........ *A61F 2/90* (2013.01); *A61F 2230/0054* (2013.01); *A61F 2240/001* (2013.01)

(58) Field of Classification Search
None
See application file for complete search history.

(56) References Cited

U.S. PATENT DOCUMENTS

| | | | | |
|---|---|---|---|---|
| 4,655,771 A | * | 4/1987 | Wallsten | A61F 2/958 606/198 |
| 5,035,706 A | * | 7/1991 | Giantureo | A61F 2/95 606/198 |
| 5,116,365 A | * | 5/1992 | Hillstead | A61F 2/90 623/1.15 |
| 5,776,162 A | * | 7/1998 | Kleshinski | A61F 2/012 606/198 |
| 6,083,257 A | * | 7/2000 | Taylor | B21F 45/00 623/1.46 |

(Continued)

FOREIGN PATENT DOCUMENTS

| | | |
|---|---|---|
| DE | 102009006180 A1 | 5/2009 |
| EP | 0744164 A1 | 11/1996 |

(Continued)

OTHER PUBLICATIONS

WIPO, U.S. International Search Authority, International Search Report and Written Opinion mailed Dec. 2, 2016 in International Patent Application No. PCT/US2016/052316, 17 pages.

(Continued)

*Primary Examiner* — Ann Hu
(74) *Attorney, Agent, or Firm* — Inskeep IP Group, Inc.

(57) ABSTRACT

A vascular prosthesis is described, having blunted wire ends. The blunted wire ends can take on a variety of configurations including end caps, bent ends, curved ends, or eyelets. The novel ends provide a smooth surface to contact the blood vessel walls thereby reducing the risk of trauma during placement of the prosthesis.

19 Claims, 7 Drawing Sheets

(56) References Cited

U.S. PATENT DOCUMENTS

| | | | | |
|---|---|---|---|---|
| 6,123,723 A * | 9/2000 | Konya | | A61F 2/07 606/108 |
| 6,214,025 B1 * | 4/2001 | Thistle | | A61F 2/0105 606/200 |
| 6,264,689 B1 * | 7/2001 | Colgan | | A61F 2/95 623/1.22 |
| 6,278,079 B1 * | 8/2001 | Mcintyre | | A61F 2/07 600/36 |
| 6,336,938 B1 * | 1/2002 | Kavteladze | | A61F 2/90 623/1.15 |
| 6,409,750 B1 * | 6/2002 | Hyodoh | | A61F 2/856 623/1.1 |
| 6,416,530 B2 * | 7/2002 | DeVries | | A61F 2/011 606/200 |
| 6,468,301 B1 * | 10/2002 | Amplatz | | A61F 2/856 623/1.13 |
| 6,632,241 B1 * | 10/2003 | Hancock | | A61F 2/90 128/898 |
| 7,300,458 B2 * | 11/2007 | Henkes | | A61B 17/12118 623/1.22 |
| 7,402,170 B2 | 7/2008 | McCullagh et al. | | |
| 7,628,806 B2 * | 12/2009 | Yampolsky | | A61F 2/07 623/1.35 |
| 7,655,039 B2 * | 2/2010 | Leanna | | D04C 1/06 623/1.53 |
| 7,785,343 B2 * | 8/2010 | Johnson | | A61F 2/01 606/200 |
| 8,197,528 B2 * | 6/2012 | Colgan | | A61F 2/90 606/198 |
| 8,313,505 B2 * | 11/2012 | Amplatz | | A61B 17/12172 606/200 |
| 8,435,285 B2 | 5/2013 | Shank et al. | | |
| 8,556,958 B2 * | 10/2013 | Wang | | A61F 2/2412 623/1.18 |
| 9,610,179 B2 * | 4/2017 | Ryan | | A61F 2/86 |
| 9,925,074 B2 * | 3/2018 | Hyodoh | | A61F 2/0105 |
| 10,335,299 B2 * | 7/2019 | Lam | | A61F 2/90 |
| 11,045,337 B2 * | 6/2021 | Lam | | A61F 2/90 |
| 11,844,528 B2 * | 12/2023 | Becking | | A61B 17/12118 |
| 2003/0144725 A1 * | 7/2003 | Lombardi | | A61F 2/07 623/1.13 |
| 2005/0256563 A1 * | 11/2005 | Clerc | | B23K 37/08 623/1.16 |
| 2007/0033789 A1 * | 2/2007 | Moriuchi | | A61F 2/91 29/282 |
| 2007/0112415 A1 * | 5/2007 | Bartlett | | A61F 2/90 623/1.15 |
| 2008/0290076 A1 * | 11/2008 | Sheldon | | A46D 1/0207 219/121.64 |
| 2009/0326637 A1 * | 12/2009 | Hashimoto | | A61F 2/86 623/1.15 |
| 2010/0217381 A1 * | 8/2010 | Paul | | A61F 2/2412 623/1.36 |
| 2012/0071964 A1 * | 3/2012 | Cattaneo | | A61F 2/90 87/9 |
| 2012/0283768 A1 * | 11/2012 | Cox | | A61B 17/1219 606/198 |
| 2013/0211492 A1 * | 8/2013 | Schneider | | A61F 2/06 623/1.11 |
| 2014/0277371 A1 * | 9/2014 | Ryan | | A61F 2/86 623/1.15 |
| 2015/0080937 A1 * | 3/2015 | Davidson | | A61F 2/01 606/200 |
| 2016/0278923 A1 * | 9/2016 | Krans | | A61F 2/2469 |
| 2018/0272044 A1 * | 9/2018 | Hossainy | | A61F 2/88 |
| 2023/0404782 A1 * | 12/2023 | Brady | | A61F 2/90 |

FOREIGN PATENT DOCUMENTS

| | | | | |
|---|---|---|---|---|
| WO | WO2000/044308 A2 | 8/2000 | | |
| WO | WO-0044308 A2 * | 8/2000 | ....... | A61B 17/12118 |
| WO | WO2011/066962 A1 | 6/2011 | | |
| WO | WO-2012087301 A1 * | 6/2012 | ............ | A61F 2/852 |
| WO | WO-2015160721 A1 * | 10/2015 | ....... | A61B 17/12031 |

OTHER PUBLICATIONS

European Patent Office, Extended European Search Report dated May 6, 2019 in European Patent Application No. 16847484.9, 7 pages.

* cited by examiner

VESSEL PROSTHESIS

RELATED APPLICATIONS

This application is a continuation of and claims priority to U.S. patent application Ser. No. 16/428,677 filed May 31, 2019 entitled Vessel Prosthesis, which is a continuation of and claims priority to U.S. patent application Ser. No. 15/268,379 filed Sep. 16, 2016 entitled Vessel Prosthesis (Now U.S. Pat. No. 10,335,299 issued Jul. 2, 2019), which claims benefit of and priority to U.S. Provisional Application Ser. No. 62/220,895 filed Sep. 18, 2015 entitled Vessel Prosthesis, all of which are hereby incorporated herein by reference in their entireties.

BACKGROUND OF THE INVENTION

Vascular prostheses such as stents and/or stent-grafts are used for a variety of reasons in the vasculature. For example, they can be used to prop open blood vessels, treat plaque buildup, replace a portion of a blood vessel, divert blood flow away from a target area, provide a scaffold or lumen for the introduction of other medical devices, or for various other reasons.

It is desirable for these devices to have significant strength and to be able to effectively anchor within a blood vessel in order to remain expanded and to prevent migration from a target area after deployment. These devices must also be track-able through a delivery device (i.e. a catheter) without too much friction so that they can be delivered to a target site. Finally, these devices must also have some flexibility in order to conform to the shape of the vessel and mimic the natural movement of the vessels.

Stents, stent-grafts, or other vascular prostheses are sometimes formed of one or more wires that are braided into a tubular structure. When these devices are braided by hand, the wire can be braided so as to terminate along the length of the stent instead of at the stent's proximal or distal ends. As a result, the hand-braided stent's ends may be relatively smooth. However, when a stent is machine-braided, its wires must typically be cut at its distal and proximal ends, creating relatively rough/sharp stent ends. Whether hand-braided or machine-braided, sharp stent ends can cause damage to the vessels as it is deployed and therefore is undesirable.

SUMMARY OF THE INVENTION

One aspect of the present invention is directed to techniques and embodiments that reduce or eliminate any relatively sharp or rough edges created from wire ends of a braided stent. For example, the wire ends of a stent can be terminated in an end cap or by bending and welding the stent's wires.

In another aspect of the present invention, a device, in particular a vascular prosthesis, in particular a stent and/or stent-graft is described. The device is comprised of one or more layers. In one embodiment, the device is comprised of metallic wires. In one embodiment, the device is comprised of two layers—an inner and an outer layer. In one embodiment, the device is comprised of two layers, where each layer is comprised of metallic wires.

The device can utilize a tie component to bind the multiple layers together. In one embodiment the tie component is comprised of one or more wires. In one embodiment the tie component is comprised of one or more radiopaque wires. The tie component can be woven in an over-under pattern relative to the multiple layers of the device.

In one embodiment, the device is comprised of an inner and outer layer. The outer layer has proximal and distal end loops or flares. The flares are comprised of wire pairs which combine to form the flares. In one embodiment, a flare cap is used to secure the wire pairs. In one embodiment, some of the flares are short and some of the flares are long. In one embodiment, the outer layer utilizes proximal and distal short and long flares. In one embodiment, the tie component generally follows the path of some of the wire(s) which comprise the flares.

In one embodiment, the device is comprised of an inner and outer layer. Both layers are comprised of wires. In one embodiment, the wires comprising the outer layer have eyelets and pairs of these eyelet-comprising wires mate with each other.

A method of making a device, in particular a stent and/or stent-graft, is described. In one embodiment, the device is wound over a mandrel with a compressed middle section and an expanded proximal and distal section. The expanded proximal and distal sections help create the flares and comprise channels to facilitate passage of the wires comprising the device. The wires can be cut at select locations to create the flares, and the wire pairs comprising the flares are bound with flare caps.

A method of using a device, in particular a prosthesis, in particular a stent and/or stent-graft is described. In one embodiment, the prosthesis is used to treat atherosclerosis where the prosthesis is used in a blood vessel to keep the blood vessel open to maintain blood flow. In one embodiment, the prosthesis is used to treat superficial femoral artery disease where the prosthesis is placed within the superficial femoral artery and/or popliteal artery

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Stents, stent-grafts, or other vascular prostheses (herein referred to as stents for simplicity) are sometimes formed of one or more wires that are braided into a tubular structure. When these devices are braided by hand, the wire can be braided so as to terminate along the length of the stent instead of at the stent's proximal or distal ends. As a result, the hand-braided stent's ends may be relatively smooth. However, when a stent is machine-braided, its wires must typically be cut at its distal and proximal ends, creating relatively rough/sharp stent ends. Whether hand-braided or machine-braided, sharp stent ends can cause damage to the vessels as it is deployed and therefore is undesirable.

One aspect of the present invention is directed to techniques and embodiments that reduce or eliminate any relatively sharp or rough edges created from wire ends of a braided stent.

Figure 1:
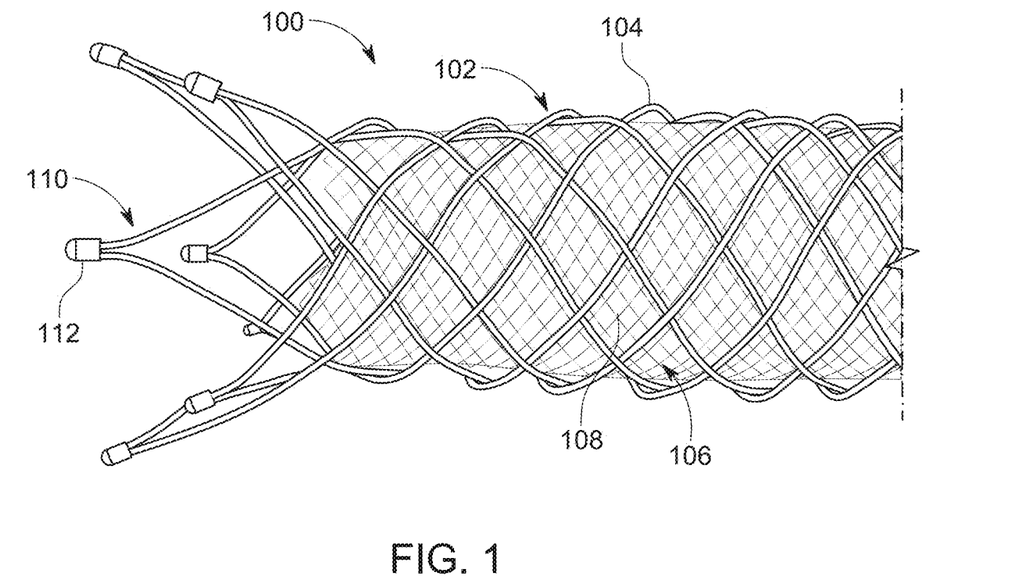
FIG. 1 illustrates an embodiment of a stent according to the present invention.
Figure 2:
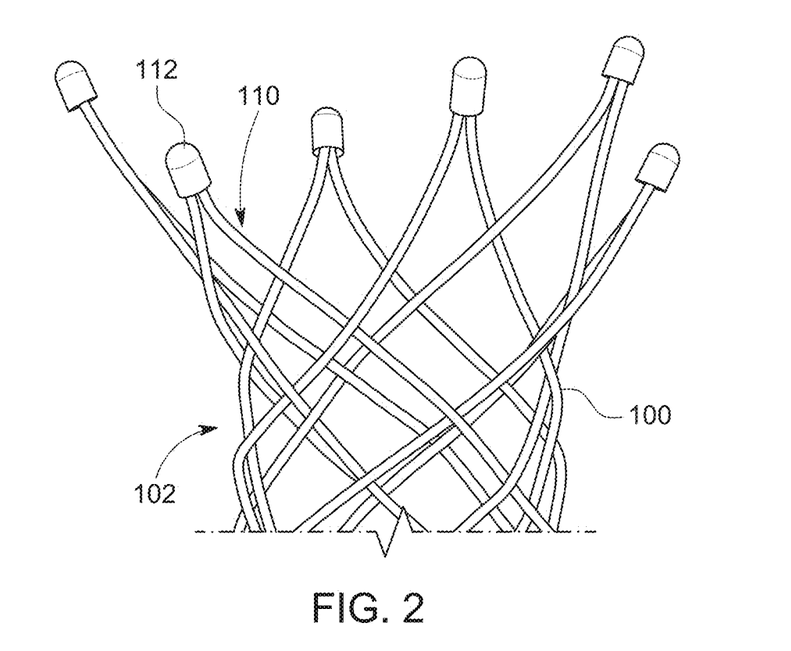
FIGS. 2-3 illustrate views of an outer layer of the stent from FIG. 1.
Figure 3:
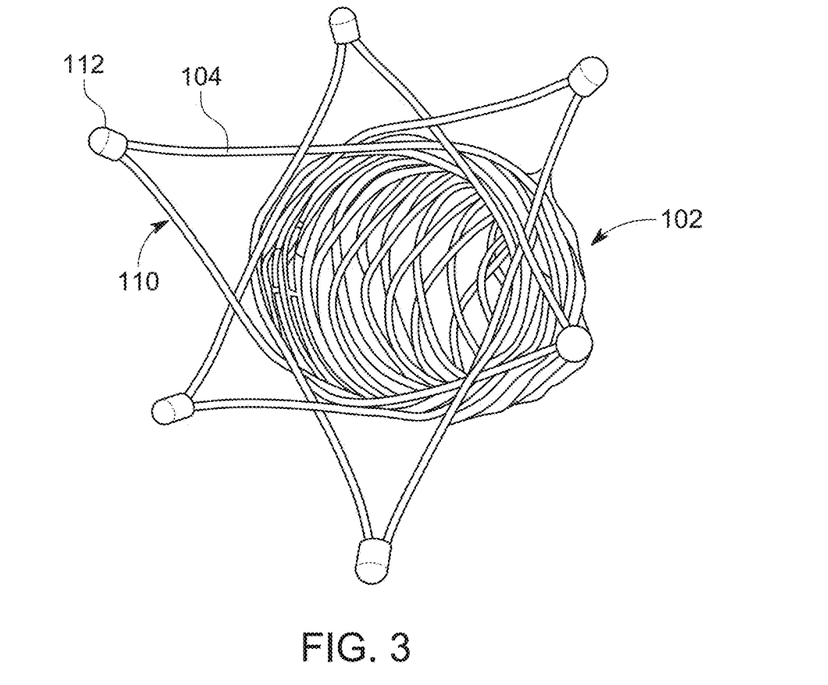

FIGS. 1-3 illustrate a braided stent 100 having distal and/or proximal ends that are rounded or blunted. Specifically, the braided stent has an outer layer 102 woven from a plurality of wires 104 that terminate with triangular or pointed loops 110. Each triangular loop 110 is preferably formed from two wires 104 that contact each other at their ends and terminate in a single end cap 112. These end caps 112 allow the ends to move freely without the complications of sharp or rough edges that would otherwise be present. These end caps 112 can also be used as a part of a delivery device to help hold and/or retrieve the stent 100 prior to full deployment where the delivery system grips the caps 112 to secure the stent 100 to the delivery system, and allow for greater retractability as described in co-pending U.S. patent application Ser. No. 15/268,271, which is incorporated by reference in its entirety.

Figure 4:
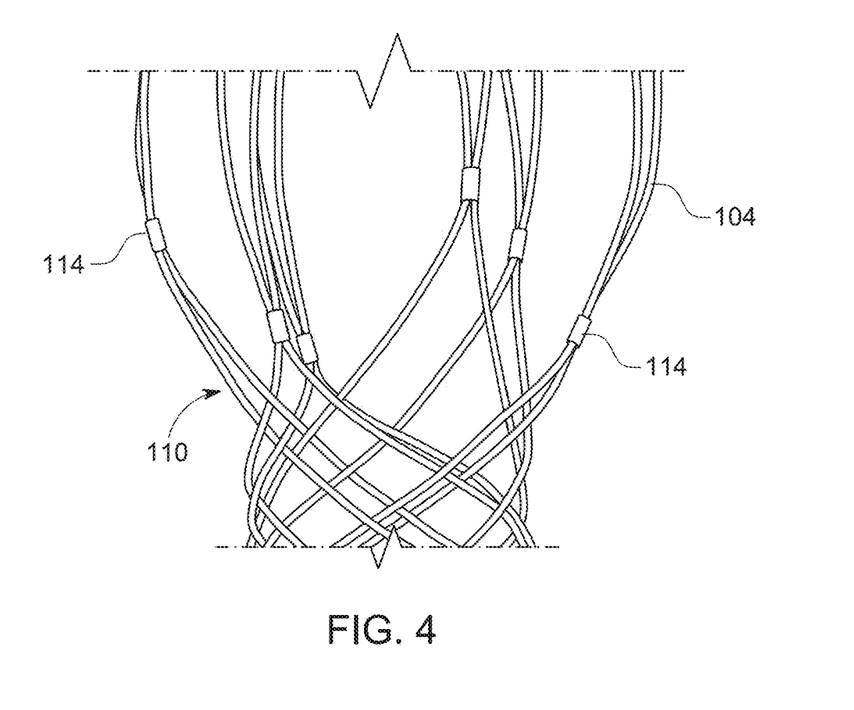
FIGS. 4-5 illustrate a technique of creating end caps for the wires of the stent from FIG. 1.
Figure 5:
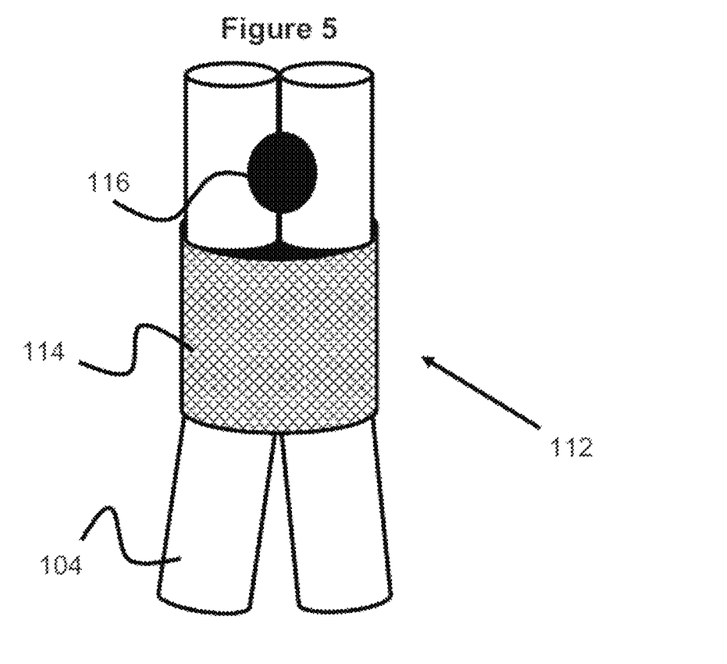

FIGS. 4 and 5 illustrate one technique of creating these triangular loops 110 and end caps 112. First, two of the wires 104 at one end of the stent 100 are moved against each other and a crimp 114 is slid or moved over the wires 104 to a desired location. The crimp 114 can be a tube or a "C" shaped structure and is preferably composed of a material suitable for welding, such as Nitinol. The crimp 114 may be further crimped or compressed around the two wires 104 after placements to help maintain its position. If the ends of the two wires 104 are not in close proximity to the top of the crimp 114, the wires 104 can be trimmed to such a level. Finally, location 116 is welded (e.g., laser welded), melting the ends of the wires 104 and the crimp 114 together until a shape resembling a rounded ball or cap results (i.e., end cap 112).

While the crimp 114 is illustrated as a tube, in an alternate embodiment it can be configured as a cap member (e.g. metallic materials such as Nitinol, or radiopaque materials such as tantalum) having an inner spaced sized for two wires 104 and a closed end. With such a cap, the wires 104 can be trimmed to a desired length, moved together, and the cap can be placed over and welded onto the wires 104. In such a configuration, the wires can either contact each other at or near the cap location or even be separated entirely—depending on the size of the cap.

Figure 6:
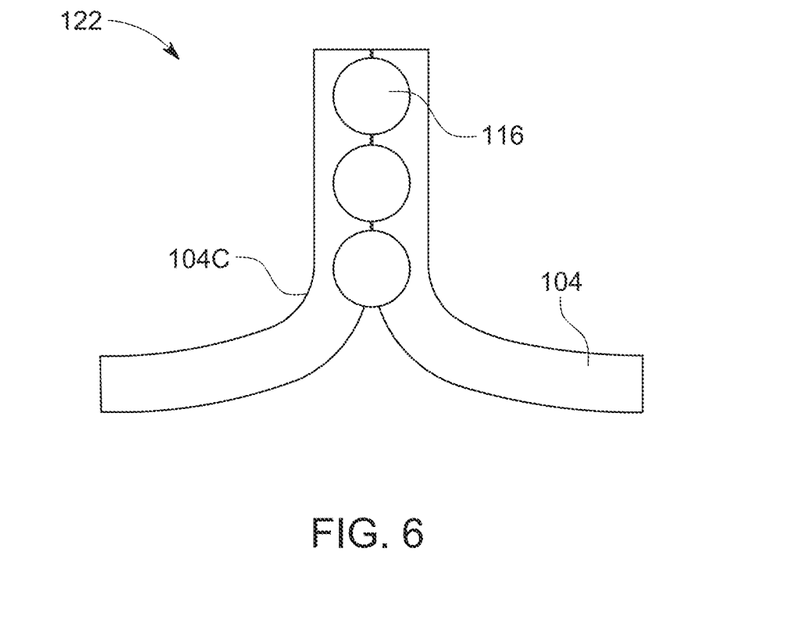
FIGS. 6-9 illustrate various alternate embodiments of blunted wire ends from a stent.

FIG. 6 illustrates an alternate technique for creating a stent 100 with blunted or smooth ends, having an end cap 122, but without a crimp 114. Symmetrical bends at locations 104C are created with the two wires 104. If necessary, the wires 104 are trimmed closely to the bend location 104C and the ends of the wires 104 near the bends 104C are welded (e.g., laser welded) at one or more weld locations 116 (e.g., three weld locations) until the wire ends resemble a rounded cap shape.

Figure 7:
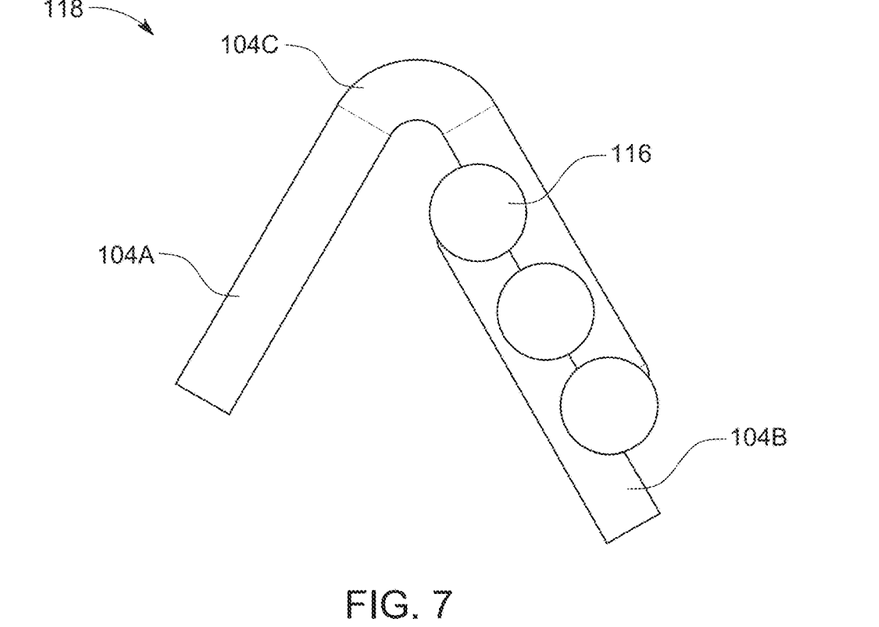

FIG. 7 illustrates another alternate technique for creating a stent 100 with blunted or smooth ends, creating a curved or bent end 118. One wire 104A is trimmed to a length that is longer than the wire 104B it is to be joined to (e.g., between 1 mm to 10 mm longer). The longer wire 104A is bent at location 104C to an angle that is preferably between, for example, about 90 and about 160 degrees so that the ends of the two wires 104A and 104B overlap when moved in proximity to each other. Finally, one or more welds are created at locations 116 (e.g., three welds).

Figure 8:
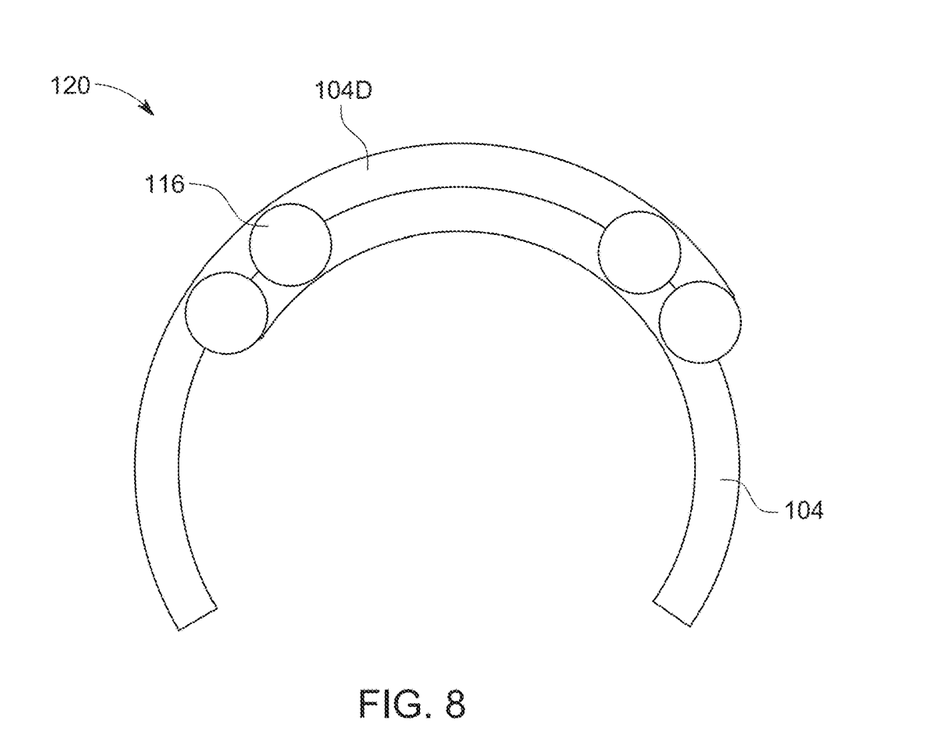

FIG. 8 illustrates yet another alternate technique for creating a stent 100 with blunted or smooth ends, creating a rounded curve 120. A curved or rounded segment 104D is created at the ends of both wires 104 that are to be joined together. These curved segments 104D are moved together and welds are created near the ends of each wire 104 at locations 116. For example, the weld locations 116 can be located between the very end of one wire 104 and a location spaced apart from the end of the other wire 104, creating two or more weld locations 116 (e.g., 4 total weld locations 116 per rounded curve 120).

Figure 9:
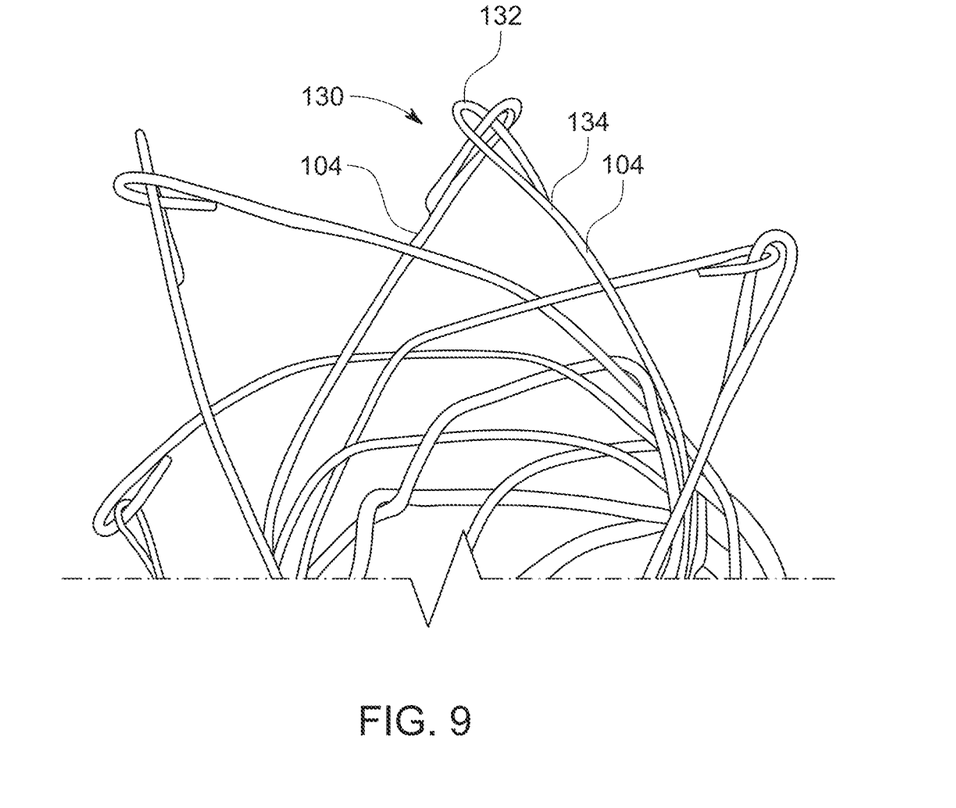

FIG. 9 illustrates yet another alternative embodiment for creating a stent 100 with blunted or smooth ends involving the use of eyelets 132. Specifically, the wires 104 comprising the outer layer of the stent 100 would utilize a wire with eyelets 132 on both the proximal and distal ends of the wires 104. The eyelets 132 may be formed by pulling the wire 104 back onto itself and welding the wire at location 134. The eyelet 132 of one wire end is first created. The second wire is then inserted into the eyelet 132 of the first wire end, and the second wire is then welded at location 134 to create the second eyelet 132 to connect the eyelets 132. The eyelets 132 allow the wires 104 to be free to move relative to each other around the eyelet region. Thus, this configuration offers some advantages in terms of flexibility of the stent 100.

Returning to FIG. 1, the stent 100 is shown as comprising two layers, an inner layer 106 and an outer layer 104 (although alternative embodiments may only have a single layer). In one embodiment, both layers are comprised of metallic wires or ribbons, such as nitinol wires. The inner layer 106 is preferably comprised of 36-60 braided wires (48 wires). The diameter of the wire 108 of the inner layer 106 can range from about 0.001" to about 0.003", such as about 0.0016" to about 0.002". The outer layer 102 is also preferably comprised of 6-24 braided or woven wires 104, such as 12 wires. The wire 104 of the outer layer 102 preferably has a diameter between about 0.004" to about 0.008", and more preferably between about 0.0055" to about 0.007".

The wires 104, 108 are preferably comprised of a metallic material such as nitinol, a radiopaque material, can be coated with radiopaque material, or can have a radiopaque core. Other materials such as cobalt-chromium or stainless steel may also be used.

As shown in the FIG. 1, the outer layer 102 is located axially outward relative to the inner layer 106. In one embodiment, the inner layer 106 is formed of a braided mesh structure with a tubular shape that is longer than the outer layer 102 and where the mesh of the inner layer 106 is cut at either or both ends.

In one embodiment, the outer layer 102 is comprised of a braided mesh of 12 wires 104 and the terminal ends (i.e. at the proximal and distal ends) of the wires 104 comprising the outer layer terminates into 6 flares or triangular loops 110. The loops 110 may all be about the same length or can vary in length. For example, the loops 110 may alternate between relatively longer loops 110 and relatively shorter loops 110, which may improve tracking through a catheter by distributing contact points to various places around the inner periphery of the catheter instead of concentrating the contact points to a few particular sections. In other words, the areas of high friction are decentralized, which improves pushing through the catheter or delivery device.

In other example embodiments, the outer layer 102 may be comprised of 8 wires and 4 triangular loops 110 at both ends or may be comprised of 16 wires with 8 triangular loops 110. The outer layer 102 and inner layer 106 may also be connected via a number of different tie mechanism, such as one or more woven wires or wire coils. Additional details of the tie components, inner/outer layers, and other aspects of the stent 100 can be found in U.S. Pub. No. 20130245745, the contents of which are hereby incorporated herein by reference. In one embodiment, the tie component is comprised of one or more wire that are weaved under the inner layer and over the outer layer of the prosthesis to bind the layers together. Alternative approaches, such as marker coils wrapped in selective locations around both the inner and outer layers, can be used in place of, or in addition to, the woven wire(s). In one embodiment, the tie component is comprised of a tantalum wire woven through the inner and outer layers of the prosthesis. In one embodiment, the tie component is comprised of a tantalum wire which follows the path of one of the wires which comprise the outer layer. Using a radiopaque material for the tie component, such as tantalum, enhances imaging of the device. Other radiopaque materials such as palladium, platinum, or gold may also be used. Non-radiopaque materials can also be used, for example a nitinol, cobalt-chromium, or stainless steel wire can be used for the tie component. Alternatively, the tie component can utilize a radiopaque core with a non-radiopaque cover or a radiopaque cover with a non-radiopaque core. Multiple tie components may also be used, where some tie components are radiopaque and some tie components are non-radiopaque. The tie component is woven in an over-under pattern with the inner and outer layer of the prosthesis to bind the layers together. The tie component can continue in this over-under pattern through the length of the prosthesis to bind the layers together. Additionally, since the tie component is preferentially made of a radiopaque material (i.e. tantalum, or other materials such as platinum, palladium, gold, etc.), the imaging of the device is augmented during delivery and placement of the prosthesis.

The actual over-under pattern can be customized depending on the properties of the prosthesis. A tighter crossing density pattern (i.e. one over followed by one under, followed by one over followed by one under, etc.) would tightly bind the inner and outer layers together and produce a stiffer prosthesis. A looser crossing density pattern (i.e. one under followed by an over pattern over several cells) would loosely bind the inner and outer layers together and produce a more flexible prosthesis.

FIGS. 10-13 illustrate tools and techniques for braiding one layer of the stent 100 (e.g., outer layer 102). The outer stent layer 102 is wound over mandrel 140, which has a smaller diameter middle region 140B and larger diameter ends 140A. The wires 104 are first placed in the longitudinal grooves 144 on one of the larger diameter ends 140. Preferably, two wires 104 are placed into each channel or groove 144 and these wire pairs are later used to later create the triangular loops 110. The wires 104 are maintained in the grooves 144 by screws 142 that screw into the larger diameter ends 140A and partially overlap on the grooves 144, thereby acting as a clamp mechanism. Once all of the desired wires 104 are clamped in the grooves 104, the outer stent layer 102 is braided over the smaller middle diameter 140B. This braiding can be achieved by hand or with braiding machine. Once the braiding is complete, the wires 104 can be clamped with screws 142 in the grooves 144 on the opposite side of the mandrel 140.

Figure 11:
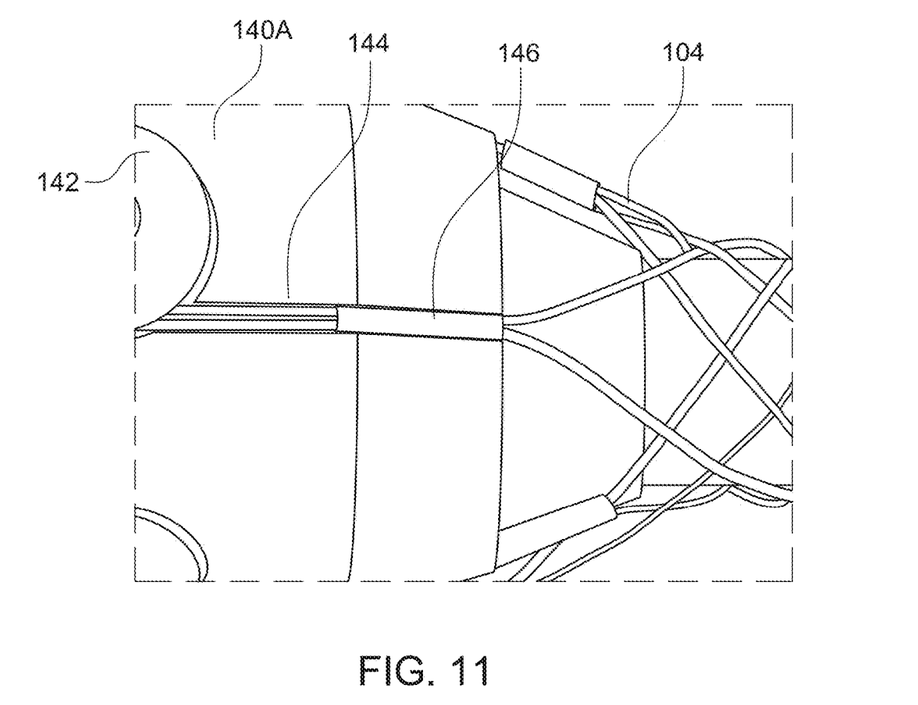

As seen in FIG. 11, tubing 146 can be placed over each pair of wires 104 to help create the location at which they come together and thereby the size of the resulting triangular loop 110. The wires can then be connected via any of the previously described techniques in this specification. For example, FIGS. 11 and 12 illustrate tubes 146 placed at longitudinally alternating positions which allows for the creation of loops 110 that alternate in size (e.g., larger, smaller, larger, smaller, etc.).

Once the desired size of the loops 110 is determined by the tube 146 location, the outer stent layer 102 is then heat set to maintain this braided configuration and size. Further electro-polishing and other manufacturing may be done as well. The outer stent layer 102 is then removed from the mandrel 140, the tubing 146 is then removed and the two wires 104 are connected via one of the previously described loop-creation techniques.

Figure 10:
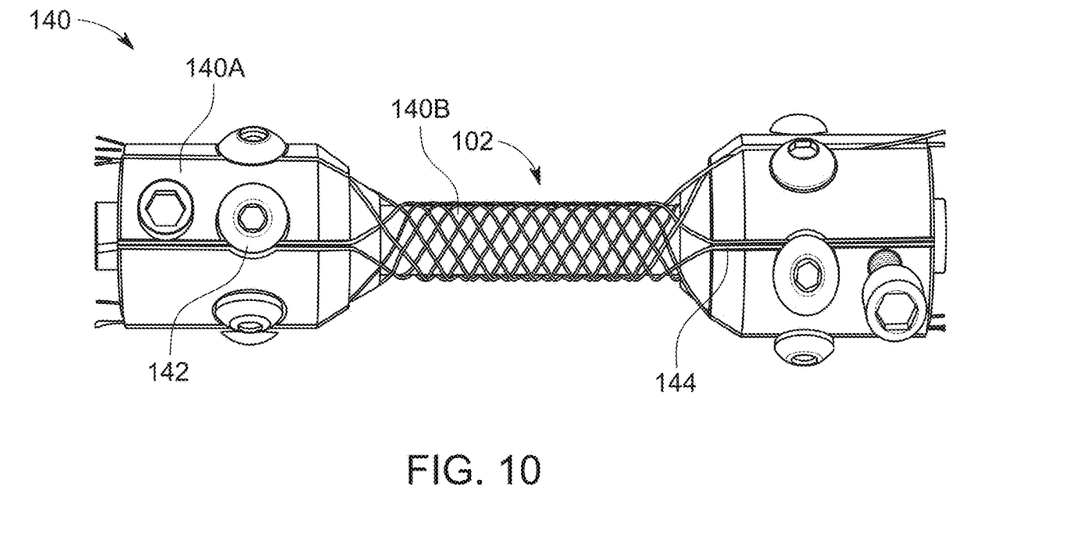
FIGS. 10-12 illustrate a mandrel for winding a stent or stent layer.
Figure 12:
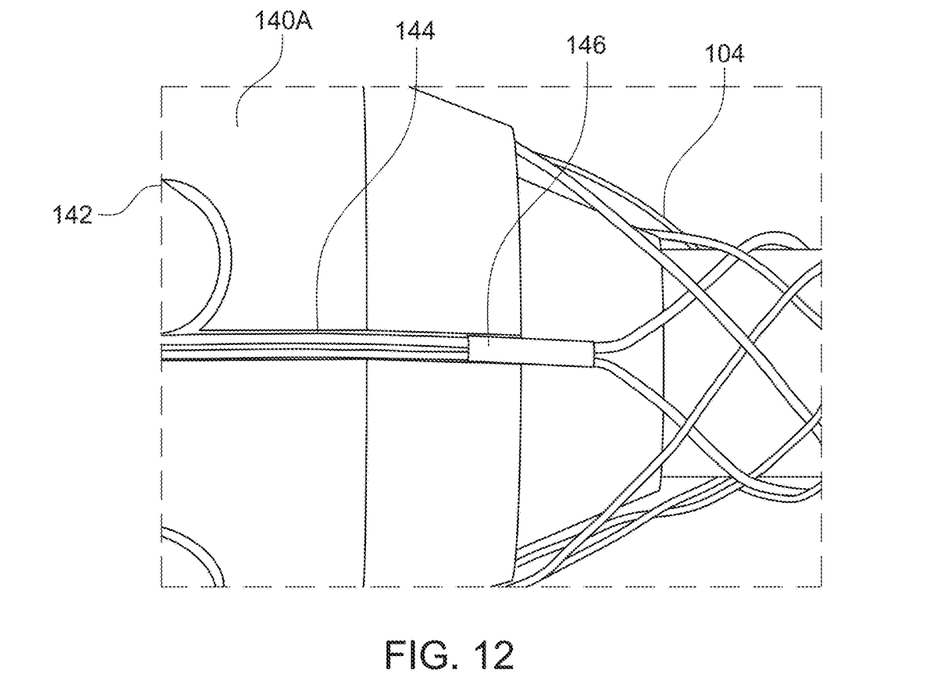
Figure 13:
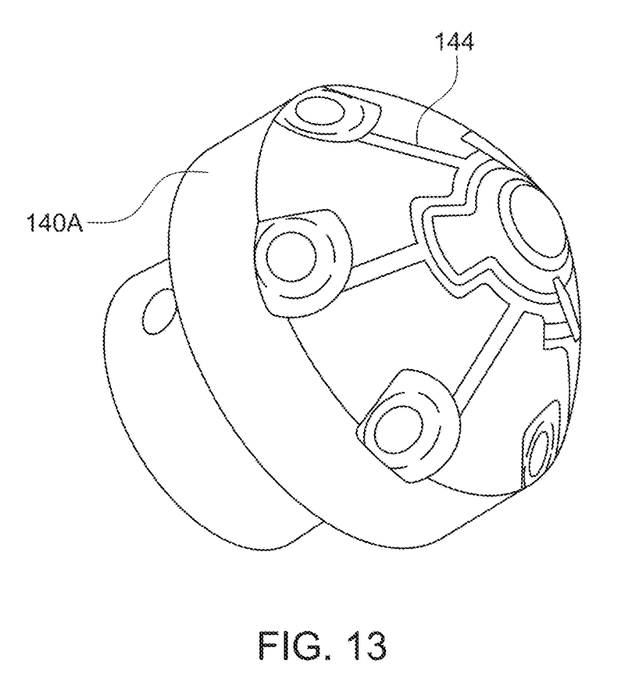
FIG. 13 illustrates an alternate embodiment of a mandrel end having grooves.

FIG. 13 shows an alternative configuration for the larger enlarged ends 104A, different from what is shown in FIGS. 10-12. In this configuration, the grooves 144 are located on a radially tapered face portion of the enlarged end, and the screw 142 (only the recess accommodating the screw is shown, but the screw 142 screws into this recess) is also on the tapered face to lock the wires 104 within the groove 144.

The inner layer 106 of the stent 100 may also be wound on a mandrel 140 having a substantially consistent diameter throughout, since the inner layer 106 has a substantially consistent diameter. The inner layer 106 is then heat set and optionally electro-polished to remove any surface irregularities. The inner layer 106 can then be placed within the outer layer and the tie component can be wound through both layers 102, 106 to bind the layers together.

The heat treatment sets the shape memory to the stent 100. In one embodiment, the stent 100 is self-expandable and has an expanded shape shape-memory. The stent 100 adopts a collapsed configuration during delivery through a delivery device (i.e. a catheter) and radially expands upon release. Though the stent 100 is self-expandable, balloons may also be used to open the stent 100.

The stent 100 described in the various embodiments, in one example, may have an overall size of about 4 millimeters to about 8 millimeters outer diameter, and a length of about 40 millimeters to about 150 millimeters.

The stent 100 is primarily described as utilizing metallic (i.e. nitinol) wires, however, other materials may be used such as stainless steel, cobalt-chromium, polymers, nitinol, and/or combinations therein may be used. Radiopaque materials such as gold, palladium, tantalum, and/or platinum may also be used, or may be used in combination with the materials described above.

The stent 100 embodiments described can be stents and/or stent-grafts used for a variety of reasons discussed earlier, such as flow diversion, propping open a vessel, treating a calcified vessel, as a scaffold use to contain additional medical devices, or similar uses. The embodiments may also be used in a variety of blood vessels sizes and locations, such as within the smaller vessels of the neuro-vasculature or within the larger vessels of the peripheral vasculature. The device can be sized appropriately based on need.

In one embodiment, the stent 100 is used to treat atherosclerotic disease, where blood vessels become calcified and must be propped open. The stent 100 helps open the blood vessel and acts as a conduit for blood flow.

In one embodiment, the stent 100 is used to treat superficial femoral artery disease. This is a disease state where arthrosclerosis, calcification, and/or plaque occurs in the peripheral vasculature, particularly in the superficial femoral artery and/or popliteal artery near the leg and knee region of the body. Please note though the terms arthrosclerosis, calcification, and plaque may technically refer to different things, they are being used synonymously here to refer generally to the build-up of unwanted or harmful matter within the blood vessel. The stent 100 may be considered a stent-graft since the prosthesis is used to mimic a portion of the vessel which is calcified. Since this artery is located near the knee, the vessels in this area flex considerably and are relatively long. A flexible stent-graft is necessary to track the movement of the vessel—however this must be combined with good anchor strength and high radial force so the prosthesis stays at the location and does not migrate. The flared ends help anchor the prosthesis in place, the inner and outer layers allow a strong scaffold to prop the blood vessel open, while the potential for a variable tie layer configuration (i.e. the over-under wound pattern described above) can customize the flexibility of the prosthesis.

A method of use of a device of the preceding embodiments involves placing a balloon in a target region with arthrosclerosis, calcification, and/or plaque and inserting and expanding a balloon in order to compress the calcification toward the vessel wall and break up some of the looser sclerotic buildup. The balloon is then deflated and removed. The stent 100 is then delivered to the target site and expanded. The stent 100 creates a scaffold to constrain the further growth of the sclerotic material, plaque, and/or calcification, and provides a flow-path for blood thus restoring flow to the vessel. In one embodiment, the device could be used in the superficial femoral artery or the popliteal arteries in the leg.

The mesh pattern of the inner layer 106 and outer layer 102 offer some advantages when used to treat plaque, calcification, and/or arthrosclerosis. Specifically, the outer layer 102 provides a strong scaffolding layer to contact the buildup, while the smaller mesh size of the inner layer 106 provides relatively small pores which sit radially inward of the outer layer 102. These small pore sizes offer a few advantages. First, they limit the amount of plaque that can be serrated or sheared by the stent 100 during placement. While it may be desirable to break up some of the undesirable matter, this is primarily done by the balloon. The stent 100 primarily acts as a scaffold to restore blood flow to the region. Any additional matter which may be sheared off by the inner or outer layer 102, 106 will likely be caught by the small pores of the inner layer 106, and there is therefore less chance of additional fragments shearing off and migrating downstream. Thus, the small pore sizes of the inner layer 106, sitting under the outer layer 102, provide another scaffolding layer to constrain additional growth of the plaque, sclerotic material, and/or calcification while allowing blood flow through the lumen of the prosthesis.

During delivery through a catheter or delivery device, the frictional contact points are limited to the outer layer 102 mesh wires 104 and the flared end components, making deliverability easier than a covered textile prosthesis in which the frictional contact is continuous throughout the length of the prosthesis. Strong radial force is achieved through the use of the outer metallic mesh layer 102, which may use larger diameter wires than the inner layer 106. The end loops 110 may offer good anchoring and retention within the vessel, to prevent the stent 100 from migrating after placement. The stent 100 also offers some degree of flexibility since the stent 100 is comprised of multiple mesh layers linked together via a tie component. The flexibility of the prosthesis can be customized by controlling the wind technique (e.g. the over-under pattern) of the tie component. A tighter tie component wind pattern would create a stiffer stent 100 where the inner and outer layers 106, 102 have limited freedom to move relative to each other. A looser tie component wind pattern would create a more flexible stent 100 where the inner and outer layers 106, 102 have more freedom to move relative to each other.

In one example, the inner layer pore size is between about 200 to about 500 micrometers. In one example, the outer layer pore size is between about 800 to about 1600 micrometers. The pore size is taken by inscribing a circle within the roughly diamond-shaped cell created by the wires comprising the respective layers.

The figures used within the specification are meant to be illustrative in nature and not restricted to what is actually shown. Similarly, any descriptive items such as measurements, materials, etc. are used for illustrative purposes to help conceptually explain the various embodiments presented herein and are not meant to be limited to what is explicitly disclosed.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vascular prosthesis comprising:
   a plurality of wires woven together to form a tubular shape, each of the plurality of wires having terminal ends;
   at least some of the terminal ends of the each of the plurality of wires being terminated with a cap having a cylindrical body and a rounded distal end;
   the cap comprising a trimmed first terminal end, a trimmed second terminal end, and a metal tube positioned flush over and melted together with the trimmed first terminal end and the trimmed second terminal end; and,
   wherein the trimmed first terminal end and the trimmed second terminal end contact each other and terminate within the cap.

2. The vascular prosthesis of claim 1, wherein the terminal ends of the plurality of wires are located at each end of the tubular shape.

3. The vascular prosthesis of claim 1, wherein the trimmed first terminal end and the trimmed second terminal end form a triangular or pointed shape.

4. The vascular prosthesis of claim 1, the trimmed first terminal end and the trimmed second terminal end form a loop.

5. The vascular prosthesis of claim 1, wherein the cap is formed of nitinol or tantalum.

6. The vascular prosthesis of claim 1, wherein the vascular prosthesis comprises an outer layer and an inner layer.

7. The vascular prosthesis of claim 1, wherein the trimmed first terminal wire end is parallel to and adjacent with the trimmed second terminal wire end within the metal tube.

8. A vascular prosthesis comprising: a plurality of wires woven together to form a tubular shape; and, a plurality of caps located at one or more ends of the tubular shape; each of the plurality of caps having a cylindrical body and a rounded distal end; and each of the plurality of caps comprising a trimmed first terminal wire end of one of the plurality of wires, a trimmed second terminal wire end of one of the plurality of wires, and a metal tube positioned flush over and melted together with the trimmed first terminal wire end and the trimmed second terminal wire end, and wherein the trimmed first terminal wire end and the trimmed second terminal wire end contact each other and terminate within the cap.

9. The vascular prosthesis of claim 8, wherein the plurality of caps is located at proximal and distal ends of the tubular shape.

10. The vascular prosthesis of claim 8, wherein the trimmed first terminal wire end and the trimmed second terminal wire end form a triangular or pointed shape.

11. The vascular prosthesis of claim 8, the trimmed first terminal wire end and the trimmed second terminal wire end form a loop.

12. The vascular prosthesis of claim 8, wherein each of the caps is formed of nitinol or tantalum.

13. The vascular prosthesis of claim 8, wherein the vascular prosthesis comprises an outer layer and an inner layer.

14. A vascular prosthesis comprising: a plurality of wires woven together to form a tubular shape; and, a plurality of caps each terminating two of the plurality of wires; each of the plurality of caps having a cylindrical body and a rounded distal end; and each of the plurality of caps comprising a trimmed first terminal wire end of one of the plurality of wires, a trimmed second terminal wire end of one of the plurality of wires, and a metal tube positioned flush over and melted together with the trimmed first terminal wire end and the trimmed second terminal wire end, and wherein the trimmed first terminal wire end and the trimmed second terminal wire end contact each other and terminate within the cap.

15. The vascular prosthesis of claim 14, wherein the plurality of caps is located at proximal and distal ends of the tubular shape.

16. The vascular prosthesis of claim 14, wherein the trimmed first terminal wire end and the trimmed second terminal wire end form a triangular or pointed shape.

17. The vascular prosthesis of claim 14, the trimmed first terminal wire end and the trimmed second terminal wire end form a loop.

18. The vascular prosthesis of claim 14, wherein each of the caps is formed of nitinol or tantalum.

19. The vascular prosthesis of claim 14, wherein the vascular prosthesis comprises an outer layer and an inner layer.

* * * * *